United States Patent
Itokawa et al.

[11] Patent Number: 5,922,838
[45] Date of Patent: Jul. 13, 1999

[54] CYCLIC HEXAPEPTIDE COMPOUNDS

[75] Inventors: Hideji Itokawa, 3-35-3, Renkoji, Tama-shi, Tokyo 206; Yukio Hitotsuyanagi, Hachioji; Takehiro Yamagishi, Tokyo, all of Japan

[73] Assignees: Taisho Pharmaceutical Co., Ltd.; Hideji Itokawa, both of Japan

[21] Appl. No.: 09/029,925

[22] PCT Filed: Sep. 10, 1996

[86] PCT No.: PCT/JP96/02570

§ 371 Date: May 5, 1998

§ 102(e) Date: May 5, 1998

[87] PCT Pub. No.: WO97/10264

PCT Pub. Date: Mar. 20, 1997

[30] Foreign Application Priority Data

Sep. 14, 1995 [JP] Japan ................... 7-236233

[51] Int. Cl.⁶ ............... A61K 38/12; C07K 7/50
[52] U.S. Cl. .............. 530/317; 530/329; 530/345; 514/10; 514/6
[58] Field of Search .............................. 530/317

[56] References Cited

U.S. PATENT DOCUMENTS 4,476,299  10/1984  Hokawa .................. 536/174

FOREIGN PATENT DOCUMENTS 58-21655   2/1983   Japan .
1180899    7/1989   Japan .
5262796   10/1993   Japan .

OTHER PUBLICATIONS

Chem Pharm. Bull, vol. 32 (1984) pp. 284–290.
Itakawa, et al. "Isolation and Anti–tumor Activity of Cyclic Hexapeptides Isolated from Rubiae Radix" Chem. Pharm. Bull., 1984, 284–290.

*Primary Examiner*—Cecilia J. Tsang
*Assistant Examiner*—Fabian A. Jameison
*Attorney, Agent, or Firm*—Lorusso & Loud

[57] ABSTRACT

Object: To provide a cyclic hexapeptide compound having a distinguished pharmaceutical effect.

Constitution: A cyclic hexapeptide compound represented by the following formula:

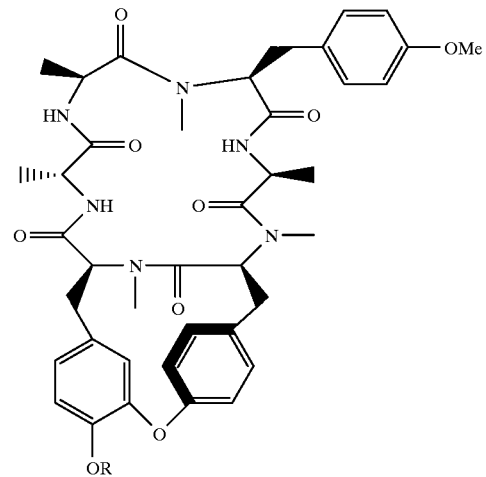

where R is a group represented by the following formula:

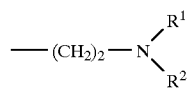

(where $R^1$ and $R^2$ are each an alkyl group, a phenyl group or a benzyl group) or a group represented by the following formula:

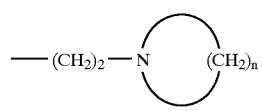

(where n is an integer of 4 to 6), or its salts.

2 Claims, No Drawings

CYCLIC HEXAPEPTIDE COMPOUNDS

TECHNICAL FIELD

The present invention relates to a cyclic hexapeptide compound having a distinguished antitumor effect and its salts.

BACKGROUND ART

Cancer now ranks at the top of causes of death and this tendency seems to last much longer. Thus, many attempts have been made to develop medicaments for curing the cancer and many researchers have engaged in studies to extract anti-tumor components from plants for a long time. For analogs of cyclic hexapeptide compounds including N-methyltyrosine and alanine of the present invention, RA-VII (TPC-B; JP-A-58-21655), RA-V (Chem. Pharm. Bull., 32, 284–290, 1984), etc., which are extracts from Rubiaceae herbs, a kind of medicinal plants, are known, among which RA-VII has been regarded as promising, but has been found not fully effective yet.

An object of the present invention is to provide a cyclic hexapeptide compound having a superior pharmaceutical effect than RA-VII.

DISCLOSURE OF THE INVENTION

The present invention provides a cyclic hexapeptide compound represented by the following formula:

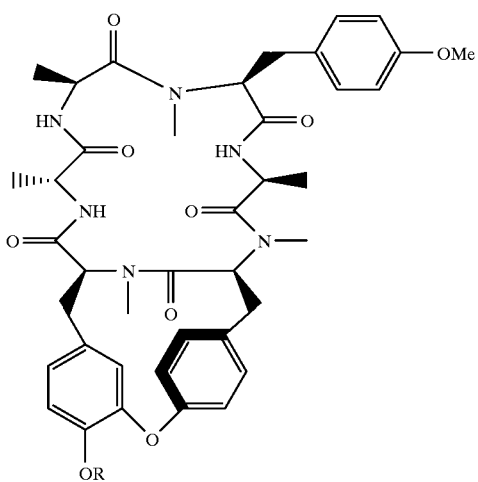

(I)

where R is a group represented by the following formula:

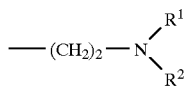

(where $R^1$ and $R^2$ are each an alkyl group, a phenyl group or a benzyl group), or a group represented by the following formula:

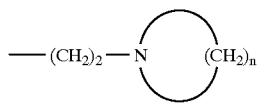

(where n is an integer of 4 to 6).

In the present invention, the alkyl group is straight or branched alkyl groups having 1 to 4 carbon atoms such as methyl, ethyl, isopropyl, n-butyl, t-butyl, etc.

The present compound can be produced in the following manner: the hydroxyl group of the compound of formula (I) wherein R is a hydrogen atom (which will be hereinafter referred to as "RA-V") is allowed to react with a nitrogen atom-containing halide, represented by the following formula:

R'–X (where R' is R other than a hydrogen atom and X is a halogen atom) to produce the present compound.

For a reaction solvent, N,N-dimethylformamide can give a good result, but dimethyl sulfoxide, 1,4-dioxane, acetone, methylethylketone, tetrahydrofuran, 1,2-dimethoxyethane, methanol, ethanol, etc. can be also used.

The reaction is carried out preferably in the presence of a base, such as potassium carbonate, sodium carbonate, potassium hydride and sodium hydride. The reaction temperature is usually in a range of 5° to 80° C., though depending upon the boiling point of a solvent.

BEST MODE FOR CARRYING OUT THE INVENTION

The present invention will be further explained below, referring to Examples. Structures and abbreviations of compounds produced in Examples are shown in Table 1.

TABLE 1

| Example No. | Abbreviation | Substituent R |
|---|---|---|
| 1 | TI-351 | Me−N−Me (with CH₂CH₂) |
| 2 | TI-356 | iPr−N−iPr (with CH₂CH₂) |
| 3 | TI-355 | Et−N−Et (with CH₂CH₂) |

TABLE 1-continued

| | | |
|---|---|---|
| 3 | TI-357 | (structure: propyl-N(benzyl)(benzyl)) |
| 3 | TI-358 | (structure: propyl-N(Et)(phenyl)) |
| 3 | TI-359 | (structure: propyl-pyrrolidinyl) |
| 3 | TI-360 | (structure: propyl-piperidinyl) |
| 3 | TI-361 | (structure: propyl-azepanyl) |

EXAMPLE 1 (TI-351)

372 mg (0.49 mmole) of RA-V and 106 mg (0.74 mmole) of 2-chloroethyldimethylamine hydrochloride are dissolved into 3 ml of N,N-dimethylformamide and then admixed with 271 mg (2.0 mmoles) of potassium carbonate with stirring at room temperature for 60 hours. Then, 1 ml of 28% aqueous ammonia is added to the reaction solution, followed by stirring at room temperature for 12 hours. Then, the reaction mixture is diluted with 20 ml of chloroform, followed by drying over anhydrous sodium sulfate. After filtration, the filtrate is concentrated under reduced pressure and the resulting residues are subjected to an alumina column chromatography. The chloroform/methanol (20:1) eluted fraction is recrystallized from methanol, whereby 198 mg of TI-351 is obtained.

m.p. 220–222° C.

$[\alpha]^{26}_D$ −205.0° (c, 0.21, CHCl$_3$)

EXAMPLE 2 (TI-356)

379 mg (0.50 mmole) of RA-V and 150 mg (0.75 mmole) of 2-chloroethyldiisopropylamine hydrochloride are dissolved into 3 ml of N,N-dimethylformamide and then admixed with 276 mg (2.0 mmoles) of potassium carbonate with stirring at room temperature for 60 hours. Then, 1 ml of 28% aqueous ammonia is added to the reaction solution, followed by stirring at room temperature for 12 hours. Then, the reaction mixture is diluted with 20 ml of chloroform and dried over anhydrous sodium sulfate. After filtration, the filtrate is concentrated under reduced pressure and the residues are subjected to an alumina column chromatography. The chloroform/methanol (50:1) eluted fraction is purified by a silica gel column chromatography and 321 mg of TI-356 is obtained from the chloroform/methanol (20:1) eluted fraction.

Amorphous powders m.p. 223–226° C. (decomposed)

$[\alpha]^{27}_D$ −182.9° (c, 0.19, CHCl$_3$)

EXAMPLE 3

TI-355, TI-357, TI-358, TI-359, TI-360 and TI-361 were synthesized from the corresponding raw material according to the procedures of Examples 1 and 2 (Table 2).

TABLE 2

| Compound | Melting point (° C.) | $[\alpha]_D$ (in CHCL$_3$) |
|---|---|---|
| TI-355 | 235 ~ 236 | −194.3° (c, 0.58) |
| TI-357 | 163 ~ 165 | −167.7° (c, 0.34) |
| TI-358 | 191 ~ 194 | −182.7° (c, 0.24) |
| TI-359 | 210 ~ 213 | −198.7° (c, 0.17) |
| TI-360 | 239 ~ 241 | −189.6° (c, 0.37) |
| TI-361 | 226 ~ 229 | −166.8° (c, 0.29) |

EXAMPLE 4

89.2 mg (0.10 mmole) of TI-356 is dissolved into 2 ml of ethanol and admixed with 0.1 ml of 2N hydrochloric acid with ice-cooling and stirring. The reaction solution is concentrated to obtain 92.4 mg of TI-356 hydrochloride.

Amorphous powders m.p. 218–221° C. (decomposed)

$[\alpha]^{23}_D$ −209.5° (c, 0.49, H$_2$O)

INDUSTRIAL APPLICABILITY

The present invention can provide a distinguished anti-tumor agent. For this purpose, the present compound can be intravenously administered upon preparation into injections using the ordinary preparation procedure. Daily dosage is 0.1–10 mg/m$^2$ and can be appropriately adjusted, depending upon patients' ages, body weights, condition, etc.

Distinguished effects of the present compound will be explained below, referring to Test Example.

Test Example [Anti-tumor effect on colon 26 (mouse colon cancer)]

A test was carried out according to the procedure disclosed in Cancer Res., 50. 2290–2295 (1990).

Colon 26 tumor tissue subcultured and transplanted on BALB/c female mice was excised from tumor-bearing mice by incision on the 11th day after the transplantation, and after removal of connective tissues it was minced with scissors. Then, 5 ml of Hank's balanced salt solution was added to 1 g of the tumor, followed by homogenization in a Luer-Lok syringe. After filtration through silicone gauze, cell number in the filtrate cell solution was counted by a hemocytometer and adjusted to 1.0 ×10$^6$ cells/ml. The resulting cell suspension was subcutaneously transplanted to CDF$_1$ male mice (aged 6 weeks, Charles River, Japan Co.) at the right axillary site at a dose of 0.2 ml/mouse to provide test tumor-bearing mice with each group consisting of 8 mice. The day of cell transplantation was designated as "day 0". TI-356 was dissolved into a surfactant (a solution of HCO 60: polyethyleneglycol =2:1), followed by slow addition of physiological saline thereto to prepare test solutions of various concentrations with the ultimate concentration being about 0.5%. The test solutions were intravenously administered from "day 3" on for 5 days.

RA-VII was used as control.

Tumor propagation-inhibiting effect was determined by measuring the principal axis and the conjugate axis of tumor by a vernier caliper on the day following the completion to administer the compound (day 8) and calculating a tumor volume, a tumor volume ratio and T/C (%) according to the following formulae. T/C of not more than 42% was judged to be effective. Results are shown in Table 3.

$$\text{Tumor volume} = \frac{(\text{principal axis}) \times (\text{conjugate axis})^2}{2}$$

$$\text{Tumor volume ratio} = \frac{\text{Tumor volume on } n\text{-th day after the start of administration } (T_n)}{\text{Tumor volume on the day of starting administration } (T_1)}$$

$$T/C\ (\%) = \frac{T_n/T_1}{C_n/C_1} \times 100$$

$C_n$: Tumor volume of control group on the $n$-th day after the start of administration $T_n$: Tumor volume of medicament-administered group on the $n$-th day after the start of administration

TABLE 3

| Test medicament | Dose (mg/kg) | T/C (%) |
|---|---|---|
| RA-VII | 1.6 | 55.8 |
| | 3.13 | 48.0 |
| | 6.25 | 49.0 |
| TI-356 | 0.8 | 42.1 |
| | 1.6 | 41.5 |
| | 3.13 | 34.5 |

We claim:

1. A cyclic hexapeptide compound represented by the following formula:

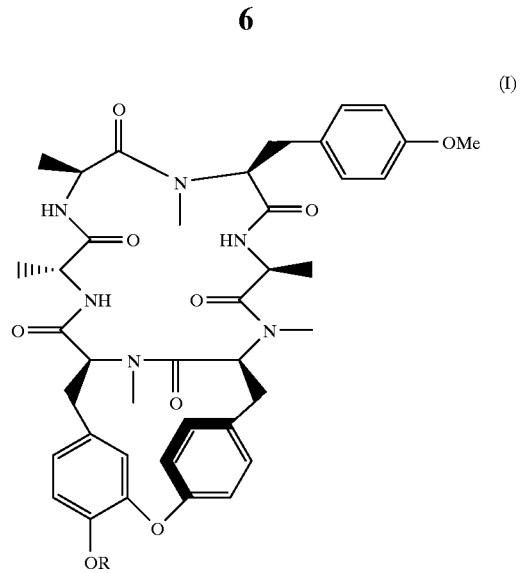

where R is a group represented by the following formula:

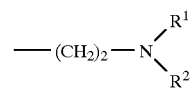

(where $R^1$ and $R^2$ are each an alkyl group, a phenyl group or a benzyl group) or a group represented by the following group:

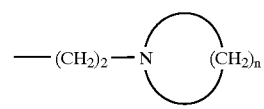

(where n is an integer of 4 to 6), or its salts.

2. A cyclic hexapeptide compound or its salts according to claim 1, wherein R of the compound (I) is a group represented by the following formula:

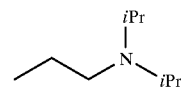

* * * * *